United States Patent
Bentzel

(10) Patent No.: US 7,775,111 B2
(45) Date of Patent: Aug. 17, 2010

(54) METHOD OF ANALYZING ULTRASONIC INSPECTION DATA FROM TURBINE WHEEL FINGER DOVETAILS TO IDENTIFY THE PRESENCE OF CRACKS ON THE FINGER LEDGES

(75) Inventor: Edward Lee Bentzel, Acworth, GA (US)

(73) Assignee: General Electric Company, Schenectady, NY (US)

( * ) Notice: Subject to any disclaimer, the term of this patent is extended or adjusted under 35 U.S.C. 154(b) by 414 days.

(21) Appl. No.: 12/047,570

(22) Filed: Mar. 13, 2008

(65) Prior Publication Data

US 2009/0229365 A1    Sep. 17, 2009

(51) Int. Cl.
*G01N 29/04* (2006.01)
(52) U.S. Cl. .............................. 73/627; 73/602; 73/628; 73/633; 73/641
(58) Field of Classification Search ............... 73/597, 73/598, 602, 625, 626, 627, 628, 633, 634, 73/637, 641
See application file for complete search history.

(56) References Cited

U.S. PATENT DOCUMENTS

| | | | | |
|---|---|---|---|---|
| 5,167,234 | A  * | 12/1992 | Watanabe et al. | 600/463 |
| 6,725,722 | B1 | 4/2004 | Murphy et al. | |
| 7,017,414 | B2 | 3/2006 | Falsetti et al. | |
| 7,302,851 | B2 * | 12/2007 | Czerw et al. | 73/620 |
| 7,337,672 | B2 * | 3/2008 | Blake et al. | 73/600 |
| 7,428,842 | B2 * | 9/2008 | Fair et al. | 73/626 |
| 7,617,733 | B2 * | 11/2009 | Deemer et al. | 73/660 |

* cited by examiner

*Primary Examiner*—J M Saint Surin
(74) *Attorney, Agent, or Firm*—Sutherland Asbill & Brennan LLP

(57) ABSTRACT

A method of analyzing ultrasonic inspection data from turbine wheel or bucket dovetail fingers for a crack about a ledge thereof with the turbine wheel or bucket having a number of adjacent holes therethrough. The method may include inserting an ultrasonic probe into a first hole, rotating an ultrasonic beam of the ultrasonic probe to scan the adjacent holes, scanning each adjacent hole, and determining the presence of the crack in the ledge by the failure to receive a signal from one or more of the adjacent holes.

20 Claims, 7 Drawing Sheets

# METHOD OF ANALYZING ULTRASONIC INSPECTION DATA FROM TURBINE WHEEL FINGER DOVETAILS TO IDENTIFY THE PRESENCE OF CRACKS ON THE FINGER LEDGES

TECHNICAL FIELD

The present application relates generally to turbines and more particularly relates to a method of inspecting turbine wheel finger dovetail ledges for cracks via the use of an ultrasonic probe.

BACKGROUND OF THE INVENTION

The rims of turbine wheels are often provided with axially spaced, annularly extending fingers that define dovetails. These dovetails receive generally complementary shaped finger dovetails on buckets that are to be secured to the wheel. A number of pinholes may be aligned axially through the bucket fingers and the wheel fingers along the margin of the wheel. The pins may be axially inserted through these pinholes to secure the buckets to the wheel.

Over time and extended use, radial loading on the pins and the presence of a corrosive environment in the turbine may cause stress corrosion cracks to develop about the pinholes. In addition, stress corrosion cracking can occur on the wheel finger ledges where the wheel fingers and bucket fingers fit together. These cracks appear to initiate mid-way between columns of pinholes on the wheel fingers. At these locations, the fingers of adjacent buckets butt together and form a crevice extending between neighboring wheel fingers. The cracks may grow circumferentially along the wheel finger ledges toward the nearest pinholes while also growing axially through the finger. These cracks may lead to the failure of a finger and potential damage to the turbine as a whole.

As a result of this possible damage, periodic inspections of the wheel and the bucket finger dovetails are indicated. These inspections generally involve driving the existing pins out of the pinholes to allow the buckets to be removed from the wheel. A florescent magnetic particle inspection of the finger surfaces or other types of inspections then may be performed. For example, the magnetic particles collect around any surface breaking cracks in the presence of an applied magnetic field. The inspector may then illuminate the area with a black light such that the magnetic particles fluoresce. Any cracks present in the finger then may be visually identified. This inspection method, however, requires extensive disassembly of the wheel and the buckets such that the method is labor intensive, time consuming, and hence, costly.

More recent improvements have led to inspecting the turbine wheel and bucket finger dovetails via a phased array ultrasonic probe inserted within a pinhole. Unlike the magnetic particle inspection, the buckets need not be removed for the ultrasonic inspection and only a fraction of the pins must be removed for probe insertion. The phased array probe is designed to produce an ultrasonic beam directed radially outward from the pinhole that is electronically rotated to inspect the surrounding finger material. A similar inspection may be performed by an ultrasonic probe in which the radially-directed beam produced by a single transducer element is rotated mechanically. This inspection method may detect cracks occurring at the adjacent pinholes and along the finger ledges. However, at the ledges the orientation of the cracks may prevent the ultrasonic beam from reflecting back to the probe. Specifically, cracks that occur on the finger ledges are generally located between adjacent pinholes and have an axial-circumferential orientation. The ultrasonic beam has an angle of incidence on these cracks that results in the beam being reflected away from the probe. Consequently, these cracks may not be identified by the same analysis method used to identify cracks occurring at the adjacent pinholes.

There is a desire, therefore, for an improved method of analyzing the ultrasonic inspection data from turbine wheel and bucket finger dovetails, particularly at the ledge region.

SUMMARY OF THE INVENTION

The present application thus describes a method of analyzing ultrasonic inspection data from turbine wheel or bucket dovetail fingers for a crack about a ledge thereof with the turbine wheel or bucket having a number of adjacent holes therethrough. The method may include inserting an ultrasonic probe into a first hole, rotating an ultrasonic beam of the ultrasonic probe to scan the adjacent holes, receiving reflected signals from each adjacent hole, and determining the presence of the crack in the ledge by the failure to receive a signal from one or more of the adjacent holes.

The present application further describes a method of analyzing ultrasonic inspection data from turbine wheel or bucket dovetail fingers for a crack about a ledge thereof with the turbine wheel or bucket having a number of adjacent holes therethrough. The method may include inserting an ultrasonic probe into a first hole, rotating an ultrasonic beam of the ultrasonic probe to scan the adjacent holes, receiving reflected signals from each adjacent hole, and determining the absence of the crack in the ledge by receiving a signal from each of the adjacent holes.

The present application further describes a method of inspecting analyzing ultrasonic inspection data from in situ turbine wheel or bucket dovetail fingers for a crack about a ledge thereof with the turbine wheel or bucket having a number of adjacent holes therethrough. The method may include the steps of removing a pin from a first hole, inserting an ultrasonic probe into the first hole, scanning each adjacent hole with a rotating ultrasonic beam, and determining the presence of the crack in the ledge by the failure to receive a signal from one or more of the adjacent holes.

These and other features of the present application will become apparent to one of ordinary skill in the art upon review of the following detailed description when taken in conjunction with the several drawings and the appended claims.

DETAILED DESCRIPTION

Figure 1:
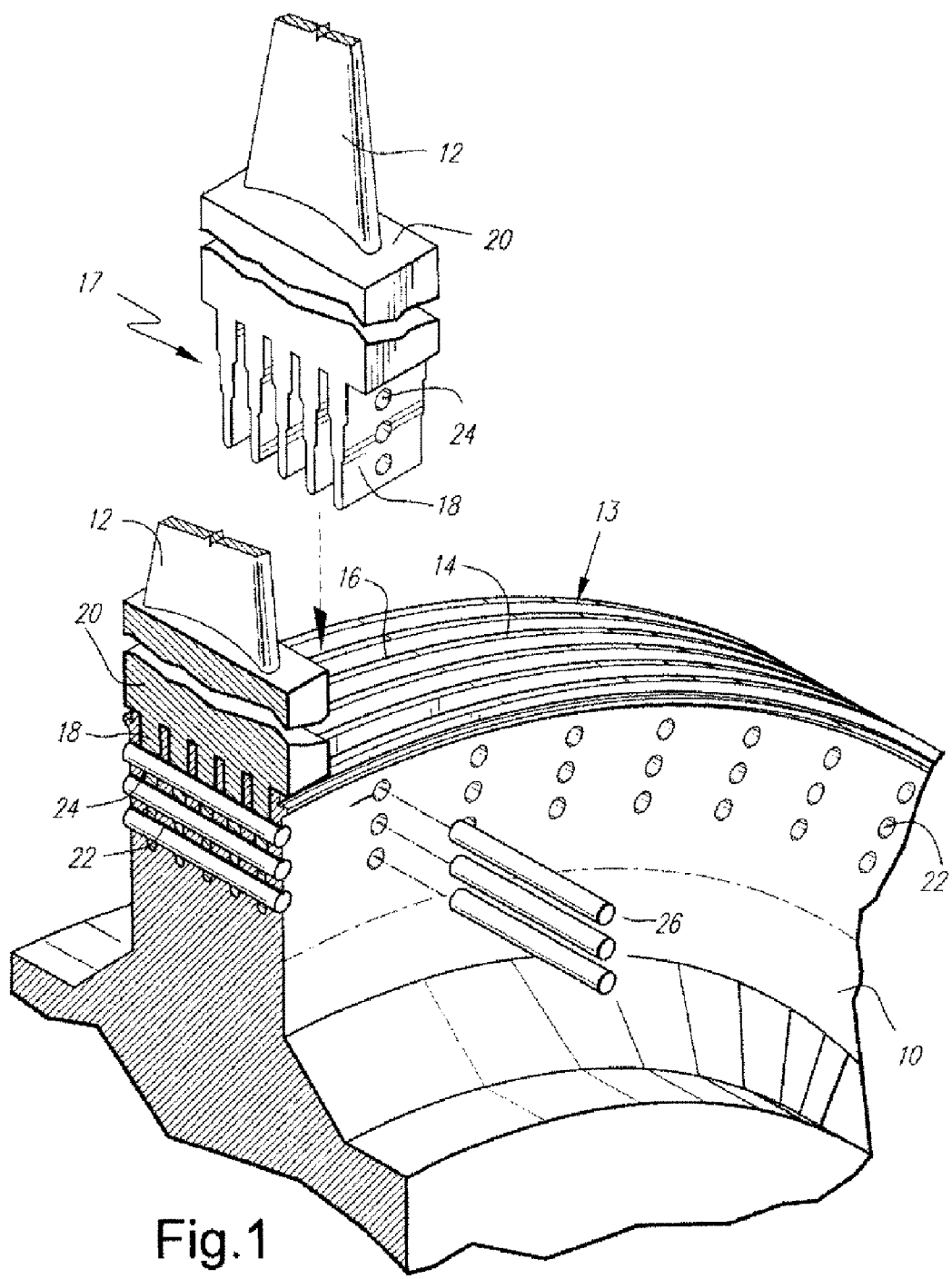
FIG. 1 is an exploded view of a turbine wheel and a bucket as may be used herein.

Referring now to the drawings, in which like numerals refer to like elements throughout the several views, FIG. 1 shows an exploded view of a rotor wheel 10 for mounting a number of buckets 12 thereon. The rotor wheel 10 includes a circumferentially extending dovetail area 13. The dovetail area 13 includes a number of circumferentially extending, radially outward projecting fingers 14. These fingers 14 define grooves 16 therebetween. The grooves 16 receive a complementary shaped dovetail 17 with a number of fingers 18 extending from a base 20.

The fingers 14, 16 of the wheel 10 and the bucket 12 have a number of axially extending pinholes, a number or wheel pinholes 22 and a number of bucket pinholes 24. Generally, columns of three (3) radially aligned holes 22, 24 are used, although any number may be used. A number of pins 26 are used to secure the buckets 12 to the wheels 10 via the pinholes 22, 24.

Figure 2:
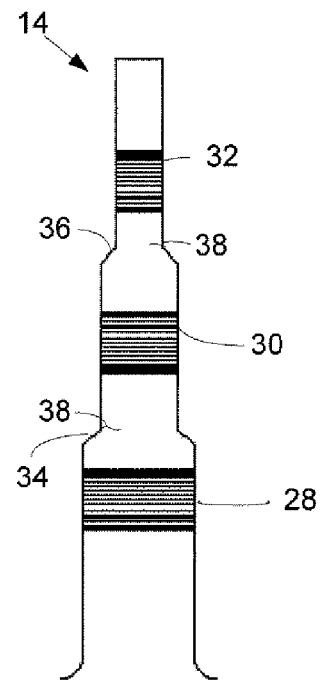
FIG. 2 is a cross-sectional view of a wheel finger of the turbine wheel of FIG. 1.

FIG. 2 shows a side cross-sectional view of a single finger 14 of the wheel 10. The wheel pinholes 22 also are shown. In this case, an inner pinhole 28, a middle pinhole 30, and an outer pinhole 32. The finger 14 also has an inner ledge 34 and an outer ledge 36. The ledges 34, 36 denote a transition in the thickness of the finger 14. As is shown, a number of cracks 38 may form at these ledges 34, 36.

Figure 4:
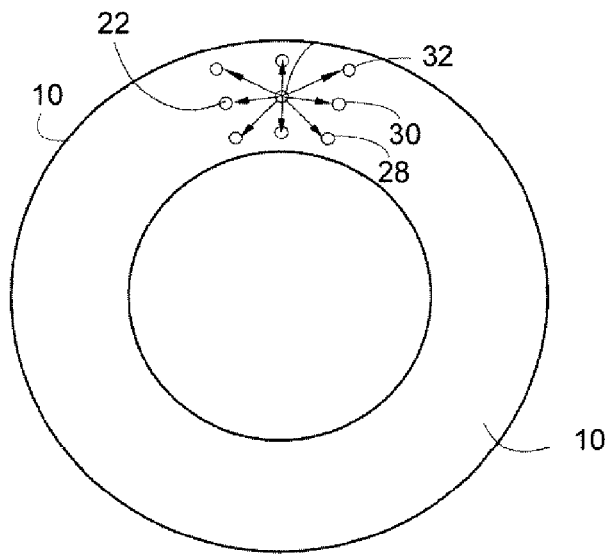
FIG. 4 is a schematic view of the beam from the ultrasonic probe as it is incident on the adjacent pinholes at different times during its rotation.
Figure 3:
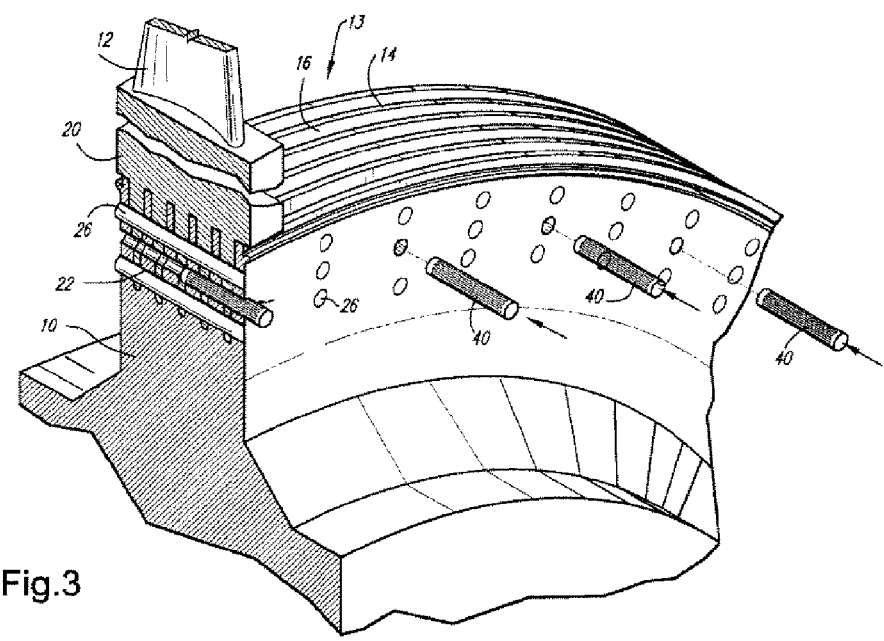
FIG. 3 perspective view of a turbine wheel and a bucket with a number of ultrasonic probes.

In the known methods, one or more of the pins 26 are removed from the pinholes 22. As is shown in FIGS. 3 and 4, a probe 40 then may be inserted into one of the wheel pinholes 22 to inspect the fingers 14 and/or fingers 18 for cracks therein. The probe 40 may be a discrete ultrasonic probe having one or more piezoelectric elements that are rotated mechanically to produce a rotating beam 41 or a phased array ultrasonic probe that electronically creates a rotating beam. The probe 40 provides a full 360-degree circumferential scan of the adjacent pinholes 22. The ultrasonic beam 41 from probe 40 continually rotates past the surface of the adjacent pinholes 22 as the probe 40 travels axially through each finger 14.

For the middle pinhole 30, there may be eight (8) adjacent pinholes 22 that surround it. In a crack-free finger 14, reflected signals 42 are received by the probe 40 from each of the eight (8) adjacent pinholes 22. The presence of a crack 38 on the inner ledge 34 or the outer ledge 36 of a finger 14, however, may block the ultrasonic beam from reaching one or more of the adjacent pinholes 22 when the crack is sufficiently deep. The result may be an absence of one or more of the reflected pinhole signals 42. Alternatively, the reference signal 42 may be reduced in amplitude and less than full strength rather than being completely blocked if the crack 38 is shallow. As such, the absence of a pinhole signal 42 or a weak pinhole signal 42 may indicate that a crack 38 is present in one of the ledges 34, 36.

Figure 5:
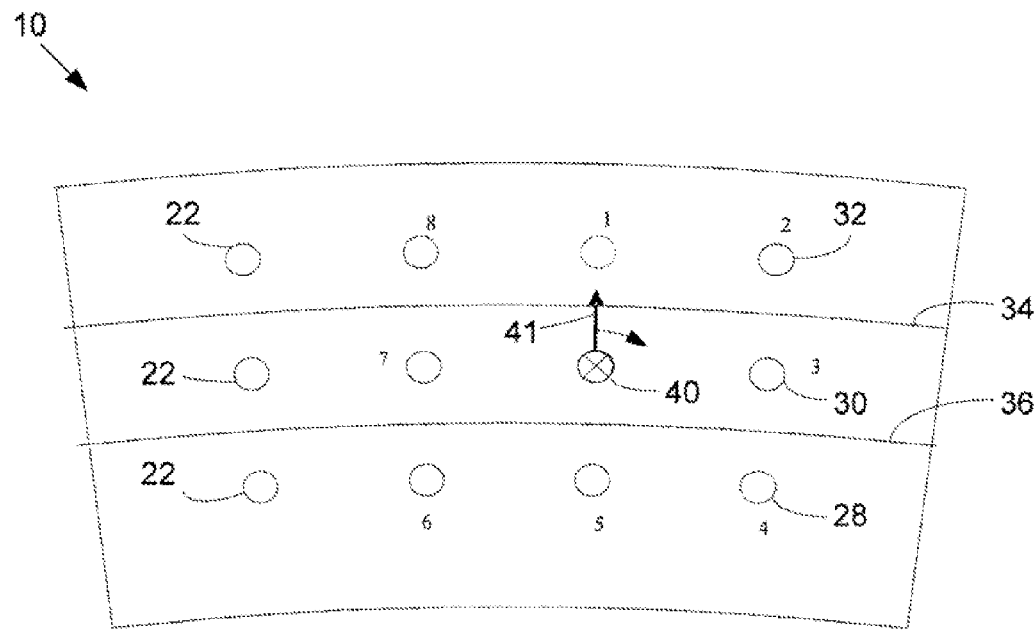
FIG. 5 is a schematic view of a turbine wheel pinhole test with the probe located in a middle pinhole and showing the ultrasonic beam and direction of beam rotation.
Figure 6:
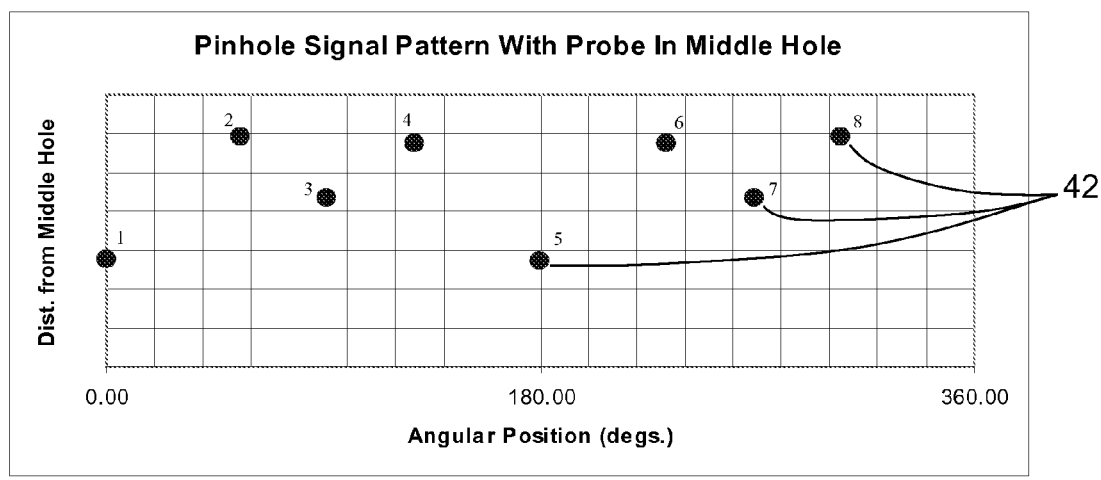
FIG. 6 is a data set showing the pattern of reflected pinhole signals of FIG. 5.

FIG. 5 shows a section of rotor wheel 10 with a number of the pinholes 22. The probe 40 is positioned within the middle pinhole 30 and a scan is taken by the probe 40 of each of the surrounding eight (8) pinholes 22. FIG. 6 shows a data set of the reflected signals 42 received by the probe 40. Specifically, signals 42 concerning each of the surrounding eight (8) pinholes 22 are received in terms of distance and angular position. In a crack-free finger 14 as is shown, data signals 42 will be received from each of the eight (8) surrounding pinholes 22.

Figure 7:
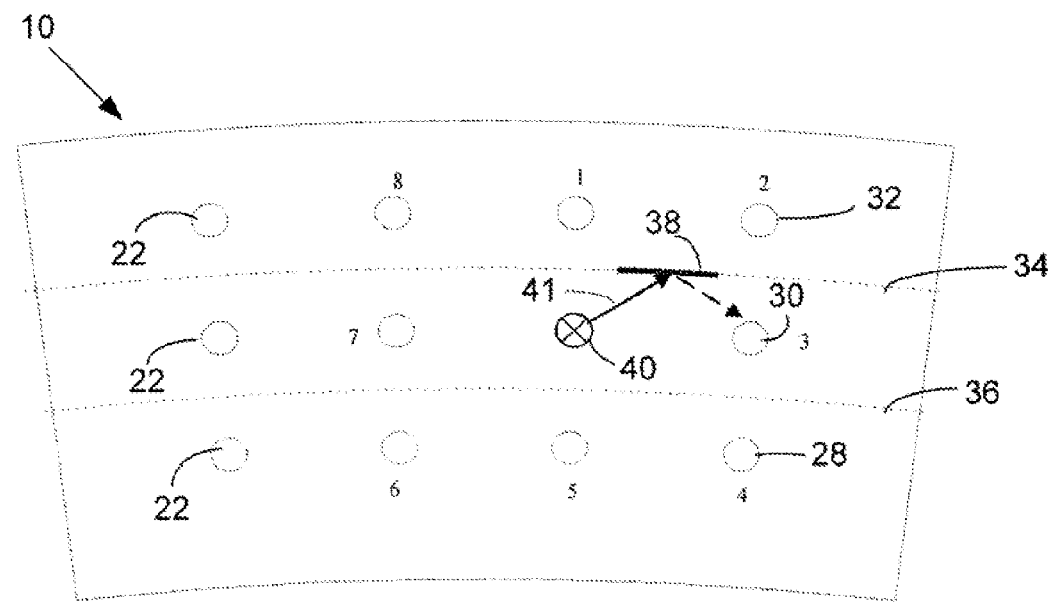
FIG. 7 is a schematic view of a turbine wheel pinhole test with a probe in the middle pinhole and crack at an outer ledge.
Figure 8:
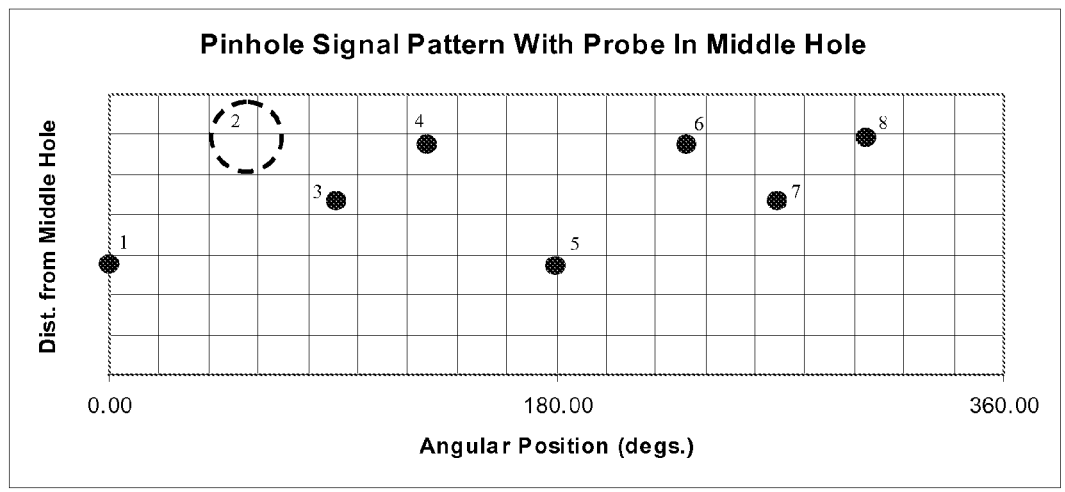
FIG. 8 is a data set showing the pattern of reflected pinhole signals of the scan of FIG. 7.
Figure 9:
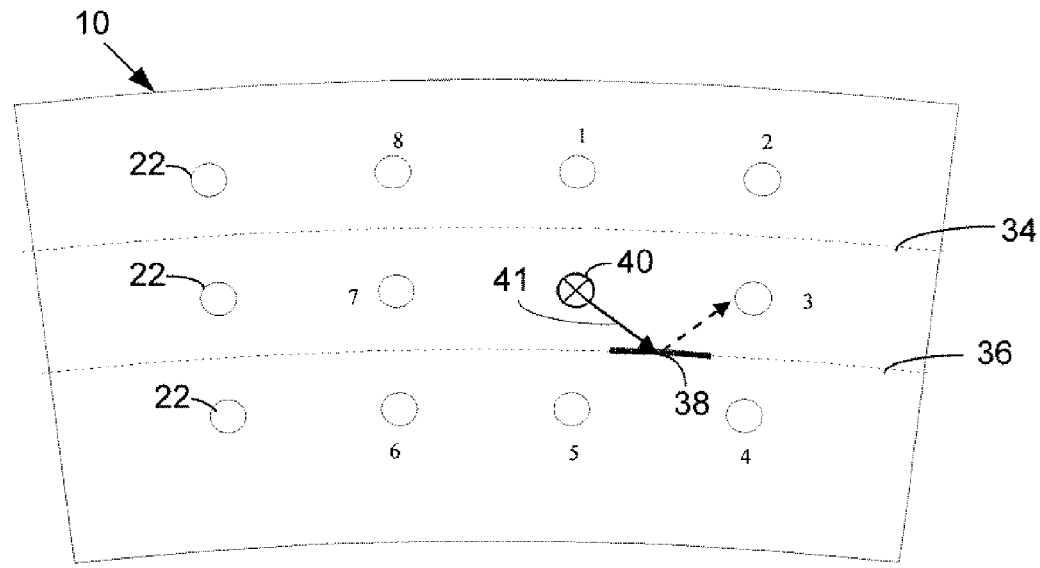
FIG. 9 is a schematic view of a turbine wheel pinhole test with a probe in the middle pinhole and a crack at an inner ledge.
Figure 10:
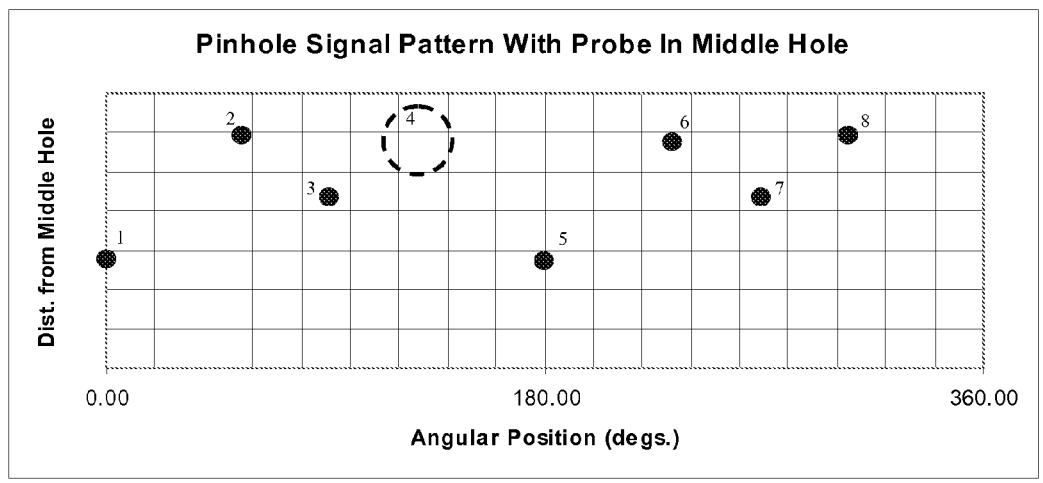
FIG. 10 is a data set showing the pattern of reflected pinhole signals of the scan of FIG. 9.

FIG. 7 shows one of the fingers 14 of the rotor wheel 10 with a crack 38 on the outer ledge 36. The probe 40 again is positioned within the middle pinhole 30 and the eight (8) surrounding pinholes 22 are scanned. FIG. 8 shows the data set of the signals 42 received by the probe 40. Given the presence of the crack 38, a signal 42 is not received from pinhole number 2 by the probe 40. Rather, the ultrasonic beam 41 is deflected by the crack 38. Likewise, a crack 38 on the inner ledge 34 is shown in FIG. 9 and the accompanying data set is shown in FIG. 10. As a result of the crack 38, the ultrasonic beam 41 is again deflected such that no data is received from pinhole number 4. The absence of a particular pinhole signal is used to determine on which ledge a crack is located. The absence of either pinhole signal number 2 or 8 in FIG. 6 indicates a crack is located on the outer ledge. Whereas the absence of pinhole signal number 4 or 6 indicates a crack is located on the inner ledge. The circumferential location of the crack along a particular ledge can also be determined from the particular pinhole signal that is absent. The absence of pinhole signal 2 indicates not only that the crack is at the outer ledge but also that it is between pinhole numbers 1 and 2, rather than between pinhole numbers 1 and 8. Likewise, the absence of pinhole number 6 indicates a crack on the inner ledge between pinhole numbers 5 and 6, rather than between pinhole numbers 4 and 5. In general, the key signals on which to concentrate are the ones from the pinholes located diagonally from the hole in which the probe is inserted and across the ledge that is being evaluated.

Figure 11:
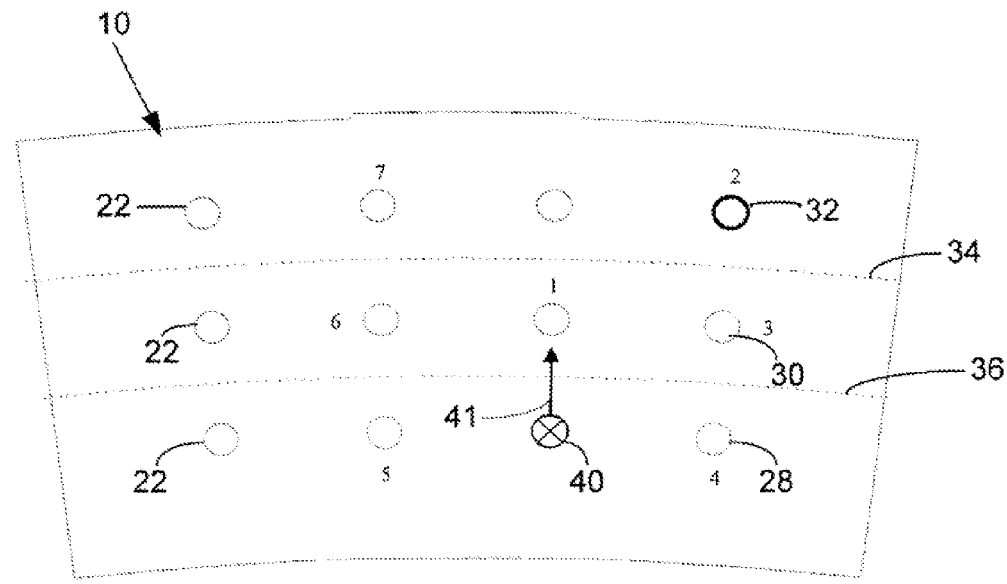
FIG. 11 is a schematic view of a turbine wheel pinhole test with the probe inserted into an inner pinhole.
Figure 12:
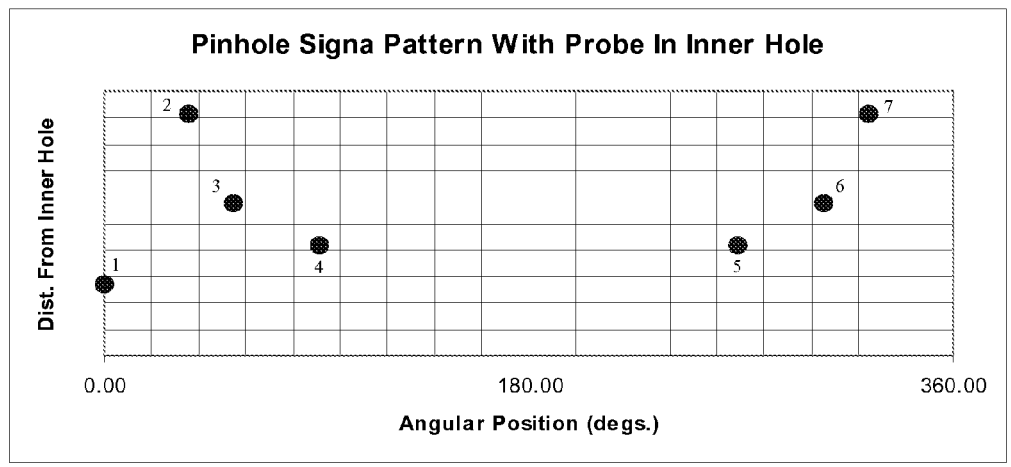
FIG. 12 is a data set showing the pattern of reflected pinhole signals of the scan of FIG. 11.
Figure 13:
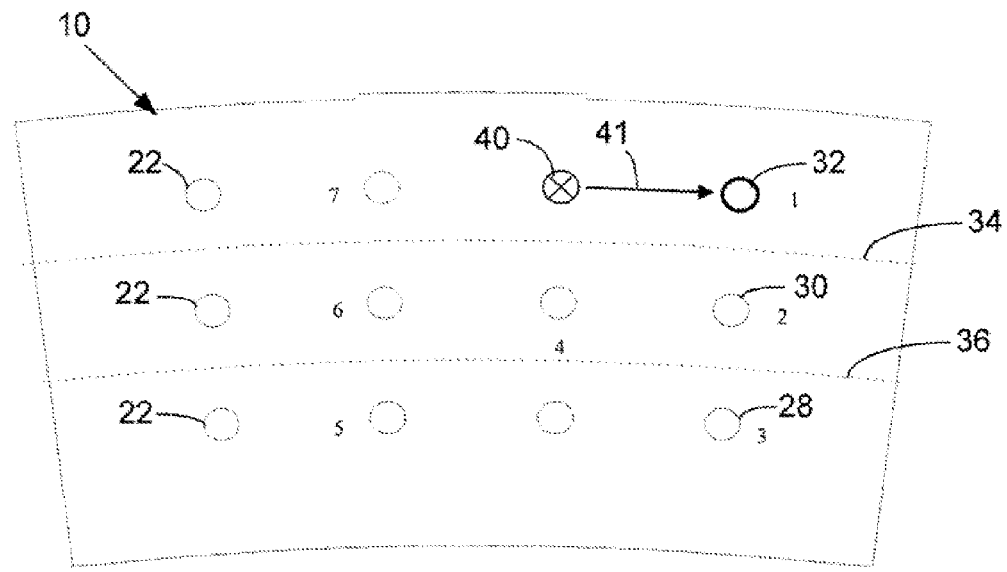
FIG. 13 is a schematic view of a turbine wheel pinhole test with the probe inserted into an outer pinhole.
Figure 14:
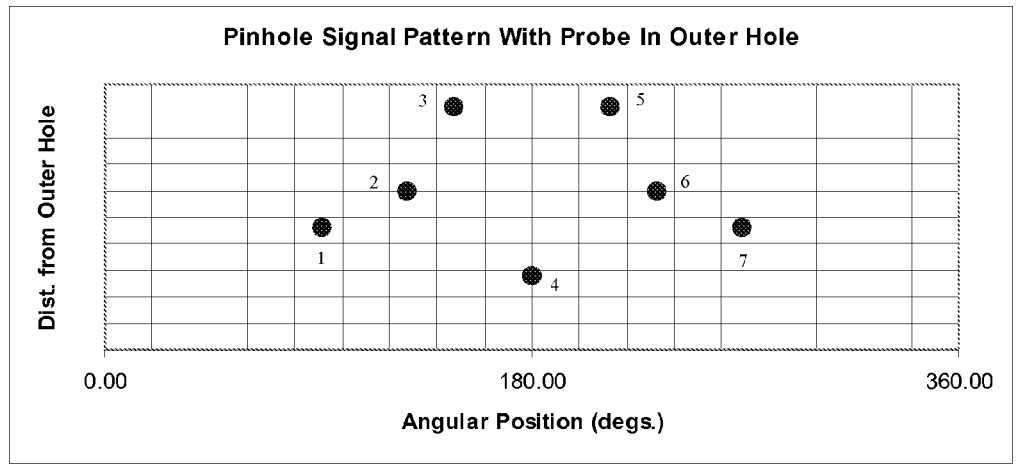
FIG. 14 is a data set showing the pattern of reflected pinhole signals of the scan of FIG. 13.

This analysis also can be used in evaluating ultrasonic data obtained with the probe 40 in an inner pinhole 28 or an outer pinhole 22. In the example of FIG. 11, with the probe 40 in inner pinhole 22 reflected signals from only seven (7) surrounding pinholes 22 would be obtained. The presence of a crack 38, however, would still be found through the absence of a signal 42. A data set from the scan of the seven (7) pinholes 22 is shown in FIG. 12. In this case, the absence of pinhole signal numbers 2 and/or 7 would indicate a crack(s) located on the outer ledge while the absence of pinhole signal numbers 3 and/or 6 would indicate a crack(s) on the inner ledge. In the example of FIG. 13, with the probe 40 in outer pinhole 22 reflected signals again from only seven (7) surrounding pinholes 22 would be obtained. The presence of a crack 38, however, would still be found through the absence of a signal 42. A data set from the scan of the seven (7) pinholes 22 is shown in FIG. 14. In this case, the absence of pinhole signal numbers 3 and/or 5 would indicate a crack(s) located on the inner ledge while the absence of pinhole signal numbers 2 and/or 6 would indicate a crack(s) on the inner ledge.

Although the techniques used herein have been described in the context of the fingers 14 of a wheel 10, the techniques are equally applicable to the fingers 18 of the bucket 12 as well. The cracks 38 in the ledges 34, 36 of the fingers 14, 18 thus may be detected by the absence of a signal 42 from the probe 40. Likewise, the techniques herein may be combined with known ultrasonic testing methods for the remaining areas of the fingers 14, 18 as are described above.

It should be apparent that the foregoing relates only to certain embodiments of the present application and that numerous changes and modifications may be made herein by one of ordinary skill in the art without departing from the general spirit and scope of the invention as defined by the following claims and the equivalents thereof.

I claim:

1. A method of analyzing ultrasonic inspection data from turbine wheel or bucket dovetail fingers for a crack about a ledge thereof with the turbine wheel or bucket having a number of adjacent holes therethrough, comprising:
   inserting an ultrasonic probe into a first hole;
   rotating an ultrasonic beam of the ultrasonic probe to scan the adjacent holes;
   receiving reflected signals from each adjacent hole; and
   determining the presence of the crack in the ledge by the failure to receive a signal from one or more of the adjacent holes.

2. The method of claim 1, wherein the number of adjacent holes includes a number of adjacent columns of three holes each and wherein the inserting step comprises inserting the probe in a middle hole of one of the columns of three holes and wherein the scanning step comprises scanning eight adjacent holes.

3. The method of claim 2, wherein determining the presence of the crack comprises receiving fewer than eight signals.

4. The method of claim 2, further comprising determining the absence of the crack by receiving eight signals.

5. The method of claim 1, wherein the number of adjacent holes includes a number of adjacent columns of three holes each and wherein the inserting step comprises inserting the probe in an outer or an inner hole of one of the columns of three holes and wherein the scanning step comprises scanning seven adjacent holes.

6. The method of claim 5, wherein determining the presence of the crack comprises receiving few than seven signals.

7. The method of claim 5, further comprising determining the absence of the crack by receiving seven signals.

8. The method of claim 1, wherein the rotating step comprises rotating about 360 degrees.

9. The method of claim 1, wherein determining the presence of the crack in the ledge by the failure to receive a signal from one or more of the adjacent holes comprises the failure to receive a signal at full strength.

10. A method of analyzing ultrasonic inspection data from turbine wheel or bucket dovetail fingers for a crack about a ledge thereof with the turbine wheel or bucket having a number of adjacent holes therethrough, comprising:
   inserting an ultrasonic probe into a first hole;
   rotating an ultrasonic beam from the ultrasonic probe to scan the adjacent holes;
   receiving reflected signals from each adjacent hole; and
   determining the absence of the crack in the ledge by receiving a signal from each of the adjacent holes.

11. The method of claim 10, wherein the number of adjacent holes includes a number of adjacent columns of three holes each and wherein the inserting step comprises inserting the probe in a middle hole of one of the columns of three holes and wherein the scanning step comprises scanning eight adjacent holes.

12. The method of claim 11, wherein determining the absence of the crack comprises receiving eight signals.

13. The method of claim 11, further comprising determining the presence of the crack by receiving less than eight signals.

14. The method of claim 10, wherein the number of adjacent holes includes a number of adjacent columns of three holes each and wherein the inserting step comprises inserting the probe in an outer or an inner hole of one of the columns of three holes and wherein the scanning step comprises scanning seven adjacent holes.

15. The method of claim 14, wherein determining the absence of the crack comprises receiving seven signals.

16. The method of claim 14, further comprising determining the presence of the crack by receiving less than seven signals.

17. The method of claim 10, wherein the rotating step comprises rotating about 360 degrees.

18. The method of claim 10, wherein determining the absence of the crack in the ledge by receiving a signal from each of the adjacent holes comprises receiving each signal at full strength.

19. A method of inspecting in situ turbine wheel or bucket dovetail fingers for a crack about a ledge thereof with the turbine wheel or bucket having a number of adjacent holes therethrough, comprising:
   removing a pin from a first hole;
   inserting an ultrasonic probe into the first hole;
   scanning each adjoining hole with a rotating ultrasonic beam; and
   determining the presence of the crack in the ledge by the failure to receive a signal from one or more of the adjacent holes.

20. The method of claim 19, wherein determining the presence of the crack in the ledge by the failure to receive a signal from one or more of the adjacent holes comprises the failure to receive a signal at full strength.

* * * * *